US006855838B2

(12) United States Patent
Haas et al.

(10) Patent No.: US 6,855,838 B2
(45) Date of Patent: Feb. 15, 2005

(54) LIPID RICH COMPOSITIONS, PRODUCTION OF LIPID RICH COMPOSITIONS, PRODUCTION OF FATTY ACID ALKYL ESTERS FROM HETEROGENEOUS LIPID MIXTURES

(75) Inventors: Michael J. Haas, Oreland, PA (US); Karen M. Scott, Ambler, PA (US); Paul J. Michalski, Horsham, PA (US); Stan Runyon, Memphis, TN (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/337,604

(22) Filed: Jan. 7, 2003

(65) Prior Publication Data

US 2003/0158074 A1 Aug. 21, 2003

Related U.S. Application Data

(60) Provisional application No. 60/347,163, filed on Jan. 9, 2002.

(51) Int. Cl.[7] .................................................. C07C 51/00
(52) U.S. Cl. ......................... 554/156; 554/157; 554/195
(58) Field of Search ................................ 554/156, 157, 554/195

(56) References Cited

U.S. PATENT DOCUMENTS

| | | | | |
|---|---|---|---|---|
| 2,383,601 | A | 8/1945 | Kelm | 260/410.9 |
| 2,494,366 | A | 1/1950 | Sprules et al. | 260/410.9 |
| 3,916,031 | A | 10/1975 | Beal | |
| 4,164,506 | A | 8/1979 | Kawahara et al. | 260/410.9 |
| 4,280,962 | A | 7/1981 | Watanabe et al. | |
| 4,695,411 | A | 9/1987 | Stern et al. | 260/410.9 |
| 4,698,186 | A | 10/1987 | Jeromin et al. | 260/421 |
| 5,298,637 | A | 3/1994 | Cooper | |
| 6,399,800 | B1 | 6/2002 | Haas et al. | 554/156 |
| 6,423,857 | B1 | 7/2002 | Copeland et al. | |
| 6,432,469 | B1 | 8/2002 | Remmercit | |

OTHER PUBLICATIONS

Notice of Publication of Application, S.N. 10/337,604, Filing Date Jan. 7, 2003.

(List continued on next page.)

*Primary Examiner*—Deborah D. Carr
(74) *Attorney, Agent, or Firm*—John D. Fado; G. Byron Stover

(57) ABSTRACT

The present invention relates to a method for producing fatty acid alkyl esters, involving esterifying a material containing free fatty acids (FFA) with an alcohol and an inorganic acid catalyst to form a product containing fatty acid alkyl esters, wherein (i) the material contains at least about 40% FFA and is produced by reacting a feedstock with steam and sulfuric acid at a pH of about 1–about 2 or (ii) the material contains at least about 80% FFA and is produced by reacting a feedstock with steam and alkali at a pH of about 11–about 13 and further reacting the feedstock with steam and sulfuric acid at a pH of about 1–about 2. The feedstock may be selected from the oils or soapstocks of soy, coconut, corn, cotton, flax, palm, rapeseed/canola, safflower, sunflower; animal fats; waste greases; and mixtures thereof; or other fully or partially hydrolyzed preparations of such feedstocks. The present invention also relates to a method for producing a lipid rich composition containing at least about 80% FFA, the method involving reacting a feedstock with steam and alkali at a pH of about 11–about 13 and further reacting the feedstock with steam and sulfuric acid at a pH of about 1–about 2. The feedstock may be selected from soy, coconut, corn, cotton, flax, palm, rapeseed/canola, safflower, sunflower, animal fats, waste greases, and mixtures thereof. The feedstock may be selected from the oils or soapstocks of soy, coconut, corn, cotton, flax, palm, rapeseed/canola, safflower, sunflower; animal fats; waste greases; and mixtures thereof; or other fully or partially hydrolyzed preparations of such feedstocks. Furthermore, the present invention concerns a lipid rich composition containing at least about 80% FFA.

31 Claims, 4 Drawing Sheets

OTHER PUBLICATIONS

Hui, Y.H., "Bailey's Industrial Oil and Fat Products", *Edible Oil and Fat Products: Processing Technology*, Fifth Edition vol. 4, pp. 56–57.

Swern, D., "Bailey's Industrial Oil and Fat Products", Fourth Edition vol. 2, pp. 290–292.

Graboski, M.S., et al., "Combustion of Fat and Vegetable Oil Derived Fuels in Diesel Engines", *Prog. Energy Combust. Sci.*, vol. 24, pp. 125–164 (1998).

Krawczyk, T., "Biodiesel", *Inform*, vol. 7(8), pp. 801–815, Aug., 1996.

Haas, M.J., et al., "Engine Performance of Biodiesel Fuel Prepared from Soybean Soapstock: A High Quality Renewable Fuel Produced from a Waste Feedstock", *Energy & Fuels*, vol. 15(5), pp. 1207–1212 (2001).

Foglia, T.A., et al., "Quantitation of Neutral Lipid Mixtures Using High Performance Liquid Chromatography with Light Scattering Detection", *J. Liquid Chrom. & Rel. Technol.*, vol. 20(12), pp. 1829–1838 (1997).

Standard Specification for Biodiesel Fuel (B100) Blend Stock for Distillate Fuels, Designation D 6751–02, American Society for Testing and Materials, West Conshohocken, PA (2002).

Peterson, C.L., et al., "Processing, Characterization, and Performance of Eight Fuels from Lipids", *Applied Engineering in Agriculture*, vol. 13(1), pp 71–79 (1997).

Freedom, B., et al., "Variables Affecting the Yields of Fatty Esters from Transesterified Vegetable Oils", *J. Am. Oil Chem. Soc.*, vol. 61(10), pp. 1638–1643, Oct., 1984.

Mittelbach, M., et al., "Diesel Fuel Derived from Vegetable Oils, Ill. Emission Tests Using Methyl Esters of Used Frying Oil", *J. Am. Oil Chem. Soc.*, vol. 65(7), pp. 1185–1187, Jul., 1998.

Haas, M.J., et al., "Enzymatic Approaches to the Production of Biodiesel Fuels", in Kuo, T.M. and Gardner, H.W. (Eds.), *Lipid Biotechnology*, Marcel Dekker, Inc., New York, pp. 587–598(2002).

Canakci, M., and J. Van Gerpen, "Biodiesel Production from Oils and Fats with High Free Fatty Acids", *Abstracts of the 92nd American Oil Chemists' Society Annual Meeting & Expo*, p. S74 (2001).

Goto et al., Pub. No.: US 2002/0077492 A1, pp. 1–5, Pub. Date: Jun. 20, 2002.

LIPID RICH COMPOSITIONS, PRODUCTION OF LIPID RICH COMPOSITIONS, PRODUCTION OF FATTY ACID ALKYL ESTERS FROM HETEROGENEOUS LIPID MIXTURES

REFERENCE TO RELATED APPLICATION

This application claims the benefit of U.S. Provisional Application No. 60/347,163, filed Jan. 9, 2002, which is incorporated herein by reference in its entirety.

BACKGROUND OF THE INVENTION

The present invention relates to a method for producing fatty acid alkyl esters, involving esterifying a material containing free fatty acids with an alcohol and an inorganic acid catalyst to form a product containing fatty acid alkyl esters, wherein (i) the material contains at least about 40% FFA and is produced by reacting a feedstock with steam and sulfuric acid at a pH of about 1–about 2 or (ii) the material contains at least about 80% FFA and is produced by reacting a feedstock with steam and alkali at a pH of about 10–about 14 and further reacting the feedstock with steam and sulfuric acid at a pH of about 1–about 2. The present invention also relates to a method for producing a lipid rich composition containing at least about 80% free fatty acids, the method involving reacting a feedstock with steam and alkali at a pH of about 10–about 14 and further reacting the feedstock with steam and sulfuric acid at a pH of about 1–about 2. Furthermore, the present invention concerns a lipid rich composition containing at least about 80% free fatty acids.

Over the past three decades interest in the reduction of air pollution, and in the development of domestic energy sources, has triggered research in many countries on the development of non-petroleum fuels for internal combustion engines. For compression ignition (diesel) engines, it has been shown that the simple alcohol esters of fatty acids (biodiesel) are acceptable alternative diesel fuels. Biodiesel has a higher oxygen content than petroleum diesel, and therefore reduces emissions of particulate matter, hydrocarbons, and carbon monoxide, while also reducing sulfur emissions due to a low sulfur content (Sheehan, J., et al., Life Cycle Inventory of Biodiesel and Petroleum Diesel for Use in an Urban Bus, National Renewable Energy Laboratory, Report NREL/SR-580-24089, Golden, Colo. (1998); Graboski, M. S., and R. L. McCormick, Prog. Energy Combust. Sci., 24:125–164 (1998)). Since it is made from agricultural materials, which are produced via photosynthetic carbon fixation (e.g., by plants and by animals that consume plants), the combustion of biodiesel does not contribute to net atmospheric carbon levels.

Initial efforts at the production, testing, and use of biodiesel employed refined edible vegetable oils and animal fats (e.g., beef tallow) as feedstocks for fuel synthesis (Krawczyk, T., INFORM, 7: 800–815 (1996); Peterson, C. L., et al., Applied Engineering in Agriculture, 13: 71–79 (1997); Holmberg, W. C., and J. E. Peeples, Biodiesel: A Technology, Performance, and Regulatory Overview, National Soy Diesel Development Board, Jefferson City, Mo. (1994)). Simple alkali-catalyzed transesterification technology (Freedman, B., et al., J. Am. Oil Chem. Soc., 61(10): 1638–1643 (1984)) is efficient at esterifying the acylglycerol-linked fatty acids of such feedstocks and is employed in making these fuels. More recently, methods have been developed to produce fatty acid methyl esters (FAME) from cheaper, less highly refined lipid feedstocks such as spent restaurant grease (Mittelbach, M., and P.

Tritthart, J. Am Oil Chem. Soc., 65(7):1185–1187 (1988); Graboski, M. S., et al., The Effect of Biodiesel Composition on Engine Emissions from a DDC Series 60 Diesel Engine, Final Report to USDOE/National Renewable Energy Laboratory, Contract No. ACG-8-17106-02 (2000); Haas, M. J., et al., Enzymatic Approaches to the Production of Biodiesel Fuels, in Kuo, T. M. and Gardner, H. W. (Eds.), Lipid Biotechnology, Marcel Dekker, Inc., New York, (2002), pp. 587–598). In addition to acylglycerols, less highly refined lipid feedstocks can contain substantial levels of free fatty acids (FFA) and other nonglyceride materials. Biodiesel synthesis from these feedstocks can be accomplished by conventional alkaline catalysis, which then requires an excess of alkali since the FFA (which are not esterified by this method) are converted to their alkali salts. These alkali salts can cause difficulties during product washing due to their ready action as emulsifiers. Ultimately, the alkali salts are removed and discarded. This approach thus involves a loss of potential product, increases catalyst expenses, and can entail a disposal cost. Alternatively, multi-step processes involving acid-catalyzed esterification of the free fatty acids and alkali-catalyzed transesterification of glyceride-linked fatty acids can be employed to achieve more efficient conversion of heterogenous feedstocks (Canakci, M., and J. Van Gerpen, Biodiesel Production from Oils and Fats with High Free Fatty Acids, Abstracts of the $92^{nd}$ American Oil Chemists' Society Annual Meeting & Expo, p. S74 (2001); U.S. Pat. Nos. 2,383,601; 2,494,366; 4,695,411; 4,698,186; 4,164,506). However, these methods can require multiple acid-catalyzed esterification steps to reduce the concentration of free fatty acids to acceptably low levels.

In addition to waste greases, other lipid-rich materials of relatively low value are potential sources of biodiesel. Among these is soapstock (SS), a coproduct of the refining of edible vegetable oils (e.g., soybean). Soapstock is an alkaline emulsion composed largely of water, acylglycerols, phosphoacylglycerols, and FFA. It is generated at a rate of about 6% of the input of unrefined oil entering a refining operation, amounting to approximately 100 million lbs annually in the United States. Although there are some industrial uses for SS, demand fluctuates and the economic return to the producer is not high, leading to interest in the development of new uses for this material.

We previously reported methods for the production of fatty acid methyl esters (FAME) from soybean SS (Haas, M. J., et al., J. Am. Oil Chem. Soc., 77:373–379 (2000)) and established that the performance and emissions properties of the resulting fuel were comparable to those of commercial biodiesel from refined soybean oil (Haas, M. J., et al., Energy & Fuels, 15(5):1207–1212 (2001)). This method for FAME synthesis employs sequential alkali-catalyzed saponification, water removal, and acid-catalyzed esterification to produce esters from both the lipid-linked and the free fatty acids of SS. The method achieves the efficient production of high purity biodiesel; however, it suffers from the fact that substantial amounts of solid sodium sulfate are generated as a byproduct. Disposal of this waste material could be cumbersome and expensive. Therefore there is a need for further development of routes for the production of fatty acid alkyl esters (e.g., FAME) from SS and similar complex lipid mixtures.

SUMMARY OF THE INVENTION

The present invention relates to a method for producing fatty acid alkyl esters, involving esterifying a material containing free fatty acids with an alcohol and an inorganic acid catalyst to form a product containing fatty acid alkyl esters, wherein (i) the material contains at least about 40% FFA and is produced by reacting a feedstock with steam and sulfuric acid at a pH of about 1–about 2 or (ii) the material contains at least about 80% FFA and is produced by reacting a feedstock with steam and alkali at a pH of about 10–about 14 and further reacting the feedstock with steam and sulfuric acid at a pH of about 1–about 2. The present invention also relates to a method for producing a lipid rich composition containing at least about 80% free fatty acids, the method involving reacting a feedstock with steam and alkali at a pH of about 10–about 14 and further reacting the feedstock with steam and sulfuric acid at a pH of about 1–about 2. The feedstock may be selected from soy, coconut, corn, cotton, flax, palm, rapeseed/canola, safflower, sunflower, animal fats, waste greases, and mixtures thereof. Furthermore, the present invention concerns a lipid rich composition containing at least about 80% free fatty acids.

DETAILED DESCRIPTION OF THE INVENTION

Figure 1A:
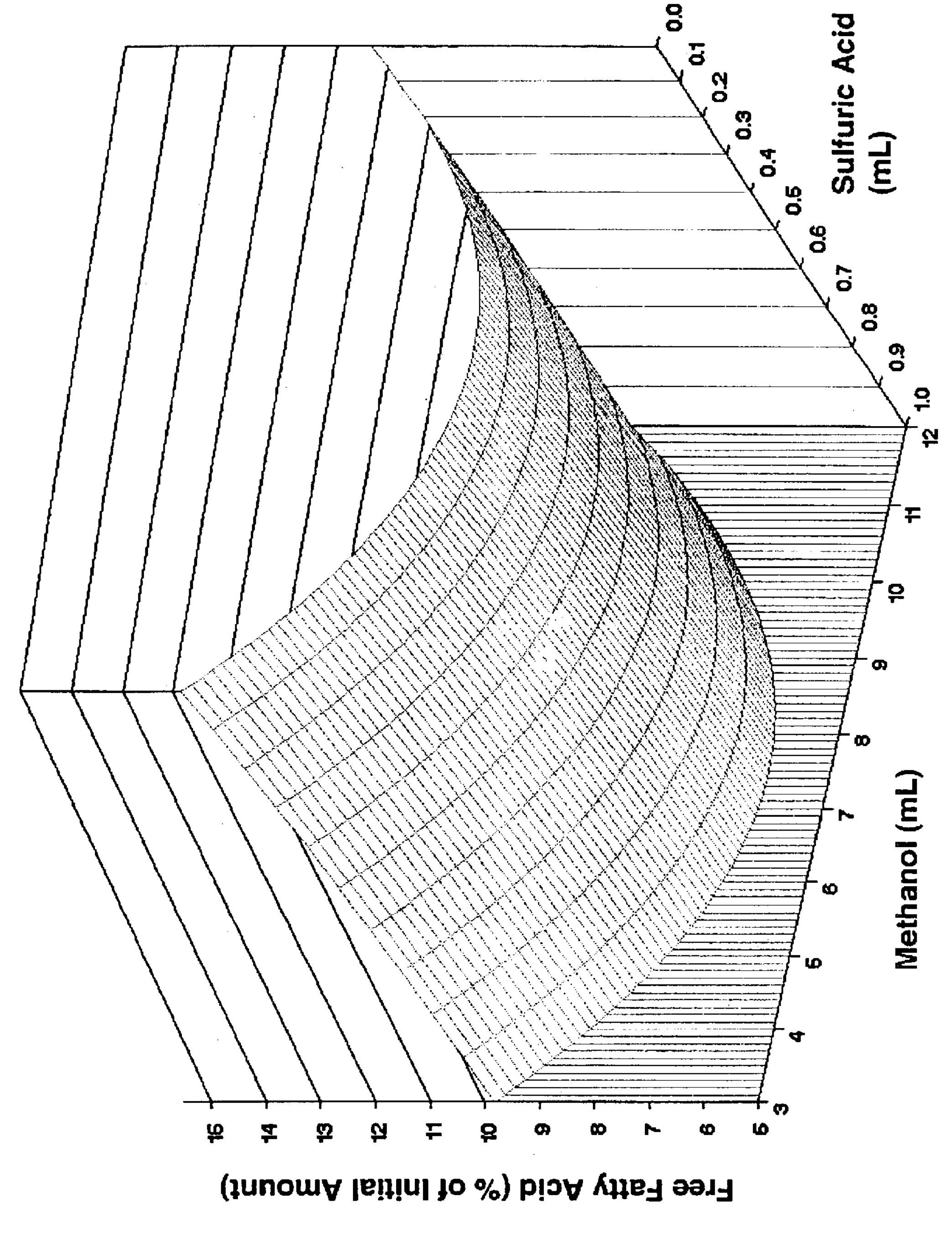
FIG. 1 shows predicted response surfaces, calculated from Equations 1–3 below, for the reduction in substrate lipid concentrations during the acid-catalyzed methyl esterification of 5.00 g soybean acid oil (described below) for 24 h at 65° C., as a function of the amounts of methanol and sulfuric acid. Extents of esterification are expressed as the percentages of unesterified species remaining relative to their content in unreacted acid oil: (A) unreacted free fatty acid, (B) unreacted diacylglycerols, (C) unreacted triacylglycerols.

The present invention relates to a method for producing fatty acid alkyl esters, involving esterifying a material containing free fatty acids with an alcohol and an inorganic acid catalyst to form a product containing fatty acid alkyl esters, wherein (i) the material contains at least about 40% FFA and is produced by reacting a feedstock with steam and sulfuric acid at a pH of about 1–about 2 or (ii) the material contains at least about 80% FFA and is produced by reacting a feedstock with steam and alkali at a pH of about 10–about 14 and further reacting the feedstock with steam and sulfuric acid at a pH of about 1–about 2. The feedstock may be selected from the oils or soapstocks of soy, coconut, corn, cotton, flax, palm, rapeseed/canola, safflower, sunflower; animal fats; waste greases; and mixtures thereof; or other fully or partially hydrolyzed preparations of such feedstocks. Thus the feedstock may be selected from the following (individually or in any combination): oils or soapstocks or other fully or partially hydrolyzed preparations of soy, coconut, corn, cotton, flax, palm, rapeseed/canola, safflower, sunflower; animal fats; waste greases; and mixtures thereof. For example, one could hydrolzye the triglycerides of tallow and use the resulting product as a feedstock. The present invention also relates to a method for producing a lipid rich composition containing at least about 80% free fatty acids, the method involving reacting a feedstock with steam and alkali at a pH of about 10–about 14 and further reacting the feedstock with steam and sulfuric acid at a pH of about 1–about 2. The feedstock may be as described above. Furthermore, the present invention concerns a lipid rich composition containing at least about 80% free fatty acids.

The process described herein is not feedstock-limited and is expected to achieve highly efficient fatty acid alkyl ester (e.g., fatty acid methyl ester) synthesis using soapstock (from crude vegetable oils) or other mixtures of vegetable lipids derived from any source of vegetable oil including, but not limited to, soy, coconut, corn, cotton, flax, palm, rapeseed/canola, safflower, and sunflower seeds or fruits; in addition, animal fats (e.g., beef tallow, poultry fat) and waste greases (generated during the deep fat frying of foods) may also be used as the feedstock. It is well known in the art that the process of working up the animal fat that comes off an animal at slaughter to the stage where it is ready for human consumption is different, chemically, than that used to refine vegetable oils, and it is termed "rendering." The preferred feedstock for the process of the present invention in the United States is soy soapstock because soybeans are the predominant oilseed processed in the United States, making soybean soapstock the predominant soapstock.

We have employed inexpensive feedstocks in the process of the present invention. One of these is soapstock, a by-product of the production and refining of edible vegetable oils. In the production of edible vegetable oils, a crude vegetable oil is first produced, often by extraction of oilseeds with hexane. To refine this crude oil, an aqueous solution of alkali (e.g., NaOH, KOH) is added (Summary and Recommendations, O. L. Brekke, T. L. Mounts, and E. H. Pryde, p. 562 in Handbook of Soy Oil Processing and Utilization, D. R. Erikson, E. H. Pryde, O. L. Brekke, T. L. Mounts, and R. A. Falb (eds.), published jointly by the American Soybean Association, St. Louis, Mo., and the American Oil Chemists' Society, Champaign, Ill., (1980)). This causes the separation of a thick emulsion known as soapstock which contains the salts of free fatty acids (soaps) that were present in the crude oil, as well as other components of the crude oil (e.g., phospholipids, pigments, tocopherols, and sterols), and some acylglycerides and water.

Typical industrial processing of SS often involves a process, termed acidulation, wherein sulfuric acid and steam are employed to achieve partial acid hydrolysis and/or removal of the acyl- and phosphoacyl-glycerol ester bonds of the starting material (Anderson, D., A Primer on Oils Processing Technology, In Bailey's Industrial Oil and Fat Products, Fifth Edition, Vol. 4, pages 1–58, edited by Y. H. Hui, John Wiley & Sons, Inc. (1996)). The acidic conditions also protonate the fatty acid (FA) salts present, greatly reducing their emulsifying properties. The heavy emulsion typical of SS is thereupon destroyed, resulting in spontaneous separation of two phases: an aqueous layer and an oil layer. The oil layer, termed acid oil, typically contains approximately 50% FFA, 30–40% tri-, di- and mono-acylglycerols, pigments and other lipophilic materials; acid oil may contain from at least about 40%-at least about 70% FFA (e.g., at least 40%-at least 70% FFA), for example at least about 40% FFA (e.g., at least 40% FFA), at least about 45% FFA (e.g., at least 45% FFA), at least about 50% FFA (e.g., at least 50% FFA), at least about 55% FFA (e.g., at least 55% FFA), at least about 60% FFA (e.g., at least 60% FFA), at least about 65% FFA (e.g., at least 65% FFA), or at least about 70% FFA (e.g., at least 70% FFA). It is used as an animal feed ingredient and a source of industrial fatty acids. Because acid oil is a readily available item of commerce, selling for approximately half the price of refined vegetable oil, we have herein explored its use as a feedstock for biodiesel production. In addition, also tested was high-acid acid oil which contained approximately 96% FFA; its production is described below. High-acid acid oil may contain from at least about 80%-at least about 98% FFA (e.g., at least 80%-at least 98%), for example at least about 80% FFA (e.g., at least 80% FFA), at least about 85% FFA (e.g., at least 85% FFA), at least about 90% FFA (e.g., at least 90% FFA), at least about 95% FFA (e.g., at least 95% FFA), at least about 96% FFA (e.g., at least 96% FFA), at least about 97% FFA (e.g., at least 97% FFA), or at least about 98% FFA (e.g., at least 98% FFA).

Generally, soybean acid oil employed herein was produced by a standard industrial acidulation method wherein concentrated sulfuric acid was added to a tank of SS, accompanied by the injection of steam, until the pH reached about 2 (pH may be about 1 to about 3; more preferably about 1.to about 2.5, most preferably about 1.6) and the temperature reached about about 82° C. to about 121° C. (e.g., 82° C. to 121° C.), more preferably about 88° C. to about 110° C. (e.g., 88° C. to 110° C.), most preferably about 105° C. (e.g, 105° C.). Steam injection was then discontinued and the resulting phases were allowed to separate by standing. The resulting clear, dark, upper liquid layer (acid oil) was recovered. To produce high-acid (HA) acid oil, the acyl- and phosphoacyl-fatty acid glyceride ester bonds of SS were alkali hydrolyzed by adding sufficient alkali to raise the pH to about 10 to about 14 (e.g., 10–14), preferably about 11 to about 14 (e.g., 11–14), more preferably about 11.5 to about 14 (e.g., 11.5–14), most preferably about 13 to about 14 (e.g., 13–14)(e.g., adding 50% (wt/vol) sodium hydroxide (or potassium hydroxide) to raise the pH of SS to about 11.6 to surprisingly produce high-acid acid oil containing about 96% FFA or raise the pH of SS to about 14 to surprisingly produce high-acid acid oil containing about 98% FFA); the mixture was heated by external steam (coils) or by steam injection to a temperature of about 66° C. to about 93° C. (e.g., 66° C. to 93° C.), more preferably about 70° C. to about 93° C. (e.g., 70° C. to 93° C.), most preferably about 93° C. (e.g., 93° C.). The mixture was then held at this temperature for between about 30 min and about 5 hr (e.g., 30 min to 5 hr), more preferably about 45 min to about 4 hr (e.g., 45 min to 4 hr), most preferably about 1 to about 2 hr (e.g., 1 to 2 hr). The mixture was then acidulated as described above for SS.

Fatty acid alkyl esters may be prepared from the fatty acids in the feedstock (e.g., acid oil or high-acid acid oil) by adding an excess (in molar terms) of an alcohol (e.g., lower alkyl alcohols, preferably methanol or ethanol) when the product is to be employed as, for example, a diesel engine fuel) and an inorganic acid (e.g., phosphoric acid or hydrochloric acid, preferably sulfuric acid). The solution is incubated with mixing in a closed container at a temperature below its boiling point for a time sufficient for the virtually quantitative esterification of the fatty acids present.

Generally, in reactions employing acid oil as the substrate, about 3–about 12 ml (e.g., 3–12 ml) of methanol per 5.0 gram of acid oil are utilized (preferably about 5–about 10 (e.g., 5–10 ml) of methanol, more preferably about 7–about 8 ml (e.g., 7–8 ml) of methanol) and about 0.1 about 2 ml (e.g., 0.1–2 ml) of sulfuric acid per 5.0 grams of acid oil (preferably about 0.5–about 1.5 ml (e.g., 0.5–1.5 ml) of sulfuric acid, more preferably about 0.8–about 1.1 ml (e.g., 0.8–1.1 ml) of sulfuric acid). The reaction time is usually about 10–about 45 hours (e.g., 10–45 hours), preferably about 15–about 35 hours (e.g., 15–35 hours), more preferably about 22–about 30 hours (e.g., 22–30 hours). The reaction temperature is usually about 50–about 72° C. (e.g., 50°–7220 C.), preferably about 55°–about 72° C. (e.g., 55°–72° C.), more preferably about 60°–about 70° C. (e.g., 60°–70° C.). The reaction can be conducted under pressure if desired, but reactions occur well in sealed containers with no applied pressure.

Generally, in reactions employing high-acid acid oil as the substrate, about 0.7–about 2.5 ml (e.g., 0.7–2.5 ml) of methanol per 5.0 gram of acid oil are utilized (preferably about 0.9–about 1.7 (e.g., 0.9–1.7 ml) of methanol, more preferably about 1.2–about 1.4 ml (e.g., 1.2–1.4 ml) of methanol) and about 0.05–about 0.3 ml (e.g., 0.05–0.30 ml) of sulfuric acid per 5.0 grams of acid oil (preferably about 0.12–about 0.25 ml (e.g., 0.12–0.25 ml) of sulfuric acid, more preferably about 0.15–about 0.19 ml (e.g., 0.15–0.19 ml) of sulfuric acid). The reaction time is usually about 2–about 25 hours (e.g., 2–25 hours), preferably about 5–about 20 hours (e.g., 5–20 hours), more preferably about 12–about 16 hours (e.g., 12–16 hours). The reaction temperature is usually about 50°–about 72° C. (e.g., 50°–72° C.), preferably about 55°–about 72° C. (e.g., 55°–72° C.), more preferably about 60°–about 70° C. (e.g., 60°–70° C.). The reaction can be conducted under pressure if desired, but reactions occur well in sealed containers with no applied pressure.

The fatty acid alkyl ester product will typically contain less than about 100 mg FFA/g fatty acid alkyl esters (e.g., less than 100 mg FFA/g fatty acid alkyl esters); the fatty acid alkyl ester product may contain less than about 60 mg FFA/g fatty acid alkyl esters (e.g., less than 60 mg FFA/g fatty acid alkyl esters), less than about 51 mg FFA/g fatty acid alkyl esters (e.g., less than 51 mg FFA/g fatty acid alkyl esters), less than about 17 mg FFA/g fatty acid alkyl esters (e.g., less than 17 mg FFA/g fatty acid alkyl esters), less than about 10 mg FFA/g fatty acid alkyl esters (e.g., less than 10 mg FFA/g fatty acid alkyl esters), or less than about 4 mg FFA/g fatty acid alkyl esters (e.g., less than 4 mg FFA/g fatty acid alkyl esters). Generally, the fatty acid alkyl ester product will contain less than about 0.1% weight basis (e.g., less than 0.1%) of unreacted triacylglycerols, unreacted diacylglycerols, and unreacted monoacylglycerols, preferably less than about 0.04% (e.g., less than 0.04%) weight basis of unreacted triacylglycerols, unreacted diacylglycerols, and unreacted monoacylglycerols. The identity of the fatty acid alkyl ester product is determined by the identity of the alcohol employed in the reaction. Preferably the fatty acid alkyl ester product is fatty acid ethyl esters or more preferably fatty acid methyl esters.

The following examples are intended only to further illustrate the invention and are not intended to limit the scope of the invention as defined by the claims.

EXAMPLES

Experimental Procedures:

Chemicals: Triolein, 1,3-diolein, 1-monoolein, and free fatty acids for use as reference standards in HPLC were obtained from Sigma (St. Louis, Mo.). Palmitic, stearic, oleic, linoleic, and linolenic acids mixed in amounts proportional to their mass abundance in soybean oil (Fritz, E., and R. W. Johnson, Raw Materials for Fatty Acids, in Fatty Acids in Industry: Processes, Properties, Derivatives, Applications, edited by R. W. Johnson and E. Fritz, Marcel Dekker. New York (1989), pp. 1–20) served as the FFA standard. A mixture of FAME whose composition reflected the fatty acid content of soy oil (RM-1) was the product of Matreya, Inc., (Pleasant Gap, Pa.). Organic solvents were B&J Brand™ High Purity Grade (Burdick & Jackson, Inc., Muskegon, Miss.). Sulfuric acid (96.3%) was the product of Mallinckrodt Baker (Paris, Ky.). t-Butyl methyl ether (99+ %, A. C. S. reagent grade) was from Aldrich (Milwaukee, Wis.). Calcium hydroxide ($Ca(OH)_2$, Codex Hydrated Lime) was obtained from Mississippi Lime Co, Alton, Ill.

Soybean acid oil was produced by standard industrial acidulation methods: concentrated sulfuric acid was added through inlet valves at the bottom of a tank of SS (25,000 gal.), accompanied by the injection of steam, until the pH reached 2. Steam injection was continued for another 2 h, then discontinued and the resulting phases were allowed to separate by standing. The resulting clear, dark, upper liquid layer (acid oil) was recovered. To produce high-acid (HA) acid oil (containing about 96% FFA), the acyl- and phosphoacyl-fatty acid glyceride ester bonds of SS were alkali hydrolyzed: solid sodium hydroxide (approx. 800 lb) was added in 50 lb portions to raise the pH of approximately 1100 gals. of SS to 11.6. Steam was injected during this process, for a total of 2.5 h. The mixture was then acidulated as described above for SS.

Optimization of esterification: Sulfuric acid-catalyzed methylation of the FFA in acid oil and HA acid oil was conducted in vigorously shaken glass screw-capped containers at 65° C. The esterification of acid oil was conducted in bottles (4.5×4.5×15 cm) and that of HA acid oil in tubes (2 cm diam.×150 mm). A Central Composite Response Surface design (Box, G. E. P., W. G. Hunter and J. S. Hunter, Statistics for Experimenters, Wiley, New York (1978)), was employed to coordinately investigate the effects and interactions of methanol and sulfuric acid concentrations and reaction time on the efficiency of esterification of the free and lipid-linked fatty acids. For HA acid oil this pattern was augmented with reactions chosen on the basis of a Box-Behnken design (Box, G. E. P., W. G. Hunter and J. S. Hunter, Statistics for Experimenters, Wiley, N.Y. (1978)) to gain further information about the effect of the variables under study on the degree of esterification. Preliminary studies (data not shown) were conducted to focus the statistically designed work in the region of variable space giving the highest ester conversions. Reactions contained 5.00 g of lipid substrate. In the esterification of acid oil, the amounts of methanol tested were 3.0, 4.8, 7.5, 10.2, and 12.0 mL; the amounts of sulfuric acid were 0.03, 0.25, 0.5, 0.80, and 1.0 mL; and reaction times were 15, 18, 22.5, 27, and 30 h. For the esterification of HA acid oil, the amounts of methanol were 0.71, 0.85, 1.07, 1.28, and 1.42 mL; the amounts of sulfuric acid were 0.1, 0.12, 0.15, 0.18, and 0.2 mL; and reaction times were 5, 8, 12.5, 17, and 20 h. Following reaction, amounts of unreacted FFA and acylglycerol were quantitated by HPLC and are expressed as a percentage of their amounts in acid oil or HA acid oil prior to esterification.

To confirm the validity of the identification of reaction conditions as optimal for the production of FAME from HA acid oil, reactions were conducted at these conditions using 20.0 gm of HA acid oil. The yield of FAME and content of unreacted lipid starting materials in the resulting product were determined. To remove the FFA, the FAME product was washed with 28% volume of 5% (wt/v) NaCl in tap water, followed by centrifugation (20 min, 4600 g). The ester layer was then washed with one-fifth volume of 4.5 M $Ca(OH)_2$ in tap water and the washed FAME product again recovered by centrifugation.

Analytical methods: To determine contents of FFA, acylglycerols and FAME, HPLC was conducted on an IB-Sil 5$\mu$ CN-BD cyanopropyl-silica column (250×4.6 mm, Phenomenex, Torrance, Calif.) essentially as described by Foglia and Jones (Foglia, T. A., and K. C. Jones, J. Liq. Chrom. & Rel. Technol., 20(12):1829–1838 (1997)). Peaks were eluted by a gradient of t-butyl methyl ether in hexane-0.4% (v/v) acetic acid, detected by ELSD, and quantitated by reference to response curves generated with standards. Most of the materials of interest were detected and quantitated using an HPLC method where the three eluting liquids were mixed from individual reservoir bottles just prior to the column. Retention times (min) were: FAME 4.3–5.0; TAG (unreacted triacylglycerols) 11.0–12.0; FFA (unreacted free fatty acids) 12.0–12.8; DAG (unreacted diacylglycerols) and phytosterols 15.5–16.3; and MAG (unreacted monoacylglycerols) 27.4–28.0. This method gave baseline separation for all species except DAG and phytosterols, which co-eluted. To quantitate DAG, glacial acetic acid was added to a final concentration of 0.4% (v/v) to the ether and hexane solutions before addition to the solvent reservoir bottles. With this solvent system, retention times were: FAME 4.3–5.0; FFA 5.0–5.2; TAG 6.7–7.2; phytosterol 13.8; DAG 15.0; MAG 28.8. This method could not be used for all analyses since the differences between the mobilities of FFA and FAME were insufficient to resolve small amounts of the former in the presence of the large amounts of the latter that were present following successful esterification. Since degrees of ester production were generally very high, esterification efficiency was expressed in terms of the amounts of each FA (fatty acid)-containing reactant remaining after incubation.

Results and Discussion:

Production of FAME from acid oil: Acid oil (typically containing 40%–60% FFA) is an established item of commerce and a potentially attractive source of FA for biodiesel synthesis. We investigated the utility of acid catalysis in the synthesis of FAME from acid oil (which contains both FFA and acylglycerols).

As received, acid oil contained (by wt) 59.3% FFA, 28.0% TAG, 4.4% DAG, and less than 1% MAG. Statistical design methods were employed to determine the effects of the methanol and sulfuric acid concentrations and length of incubation at 65° C. on the degree of esterification of the free- and glyceride-linked fatty acids in acid oil. Incubation times were limited to a maximum of approximately 24 h as this was felt to be the longest duration suited to an industrial operation. Equations 1–3 present the equations of the best-fit second-order response surfaces describing the relationships between the reaction variables examined and the percentages of remaining unesterified FFA, TAG, and DAG. Monoacylglycerols were not detected following esterification.

$$FFA=40.80-2.98\ M-4.35\ A-1.88\ T+0.16\ MA+0.06\ AT+0.18\ M^2+0.48\ A^2+0.04\ T^2 \quad (1)$$

$$TAG=193.3-11.25\ M-134.2\ A-7.00\ T+7.73\ MA+0.03\ MT+0.87\ AT+0.27\ M^2+30.06\ A^2+0.12\ T^2 \quad (2)$$

$$DAG=209.7-18.43\ M-107.9\ A-6.8\ T+7.46\ MA+0.13\ MT+0.69\ AT+0.56\ M^2+14.33\ A^2+0.10\ T^2 \quad (3)$$

where (all terms are expressed as wt % of their mass in unreacted starting material): FFA=unreacted free fatty acid; TAG=unreacted triacylglycerols; DAG=unreacted diacylglycerols; M=methanol (mL per 5.00 g input acid oil); A=sulfuric acid (mL per 5.00 g input acid oil); and T=incubation time (h). The $R^2$ values for these equations were 0.91 to 0.92, indicating acceptable fits to the experimental data.

FIG. 1 shows the dependence of the amounts of residual unesterified FFA, DAG and TAG on reaction conditions in the esterification of acid oil, derived from Equations 1–3.

Figure 1B:
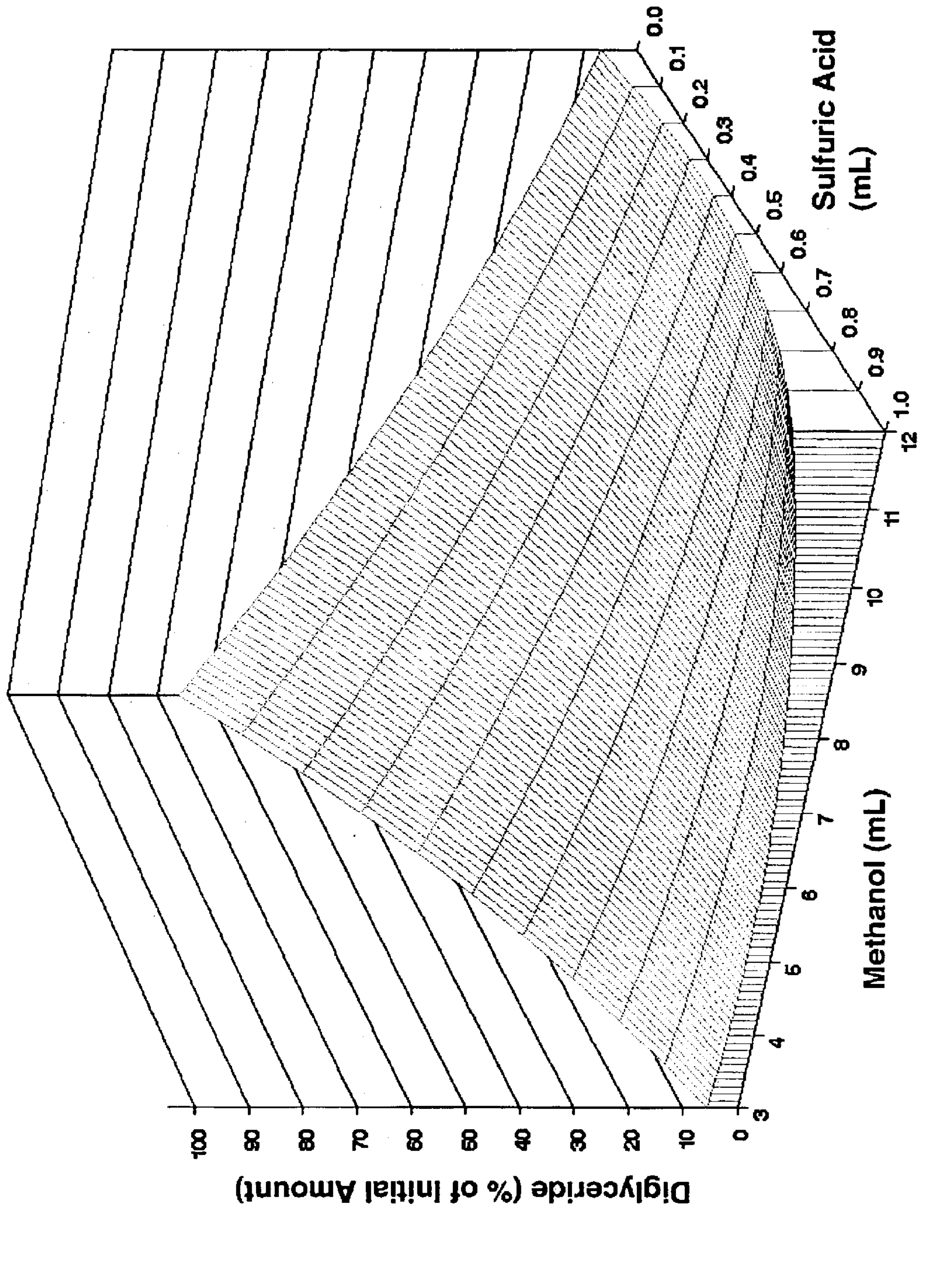
Figure 1C:
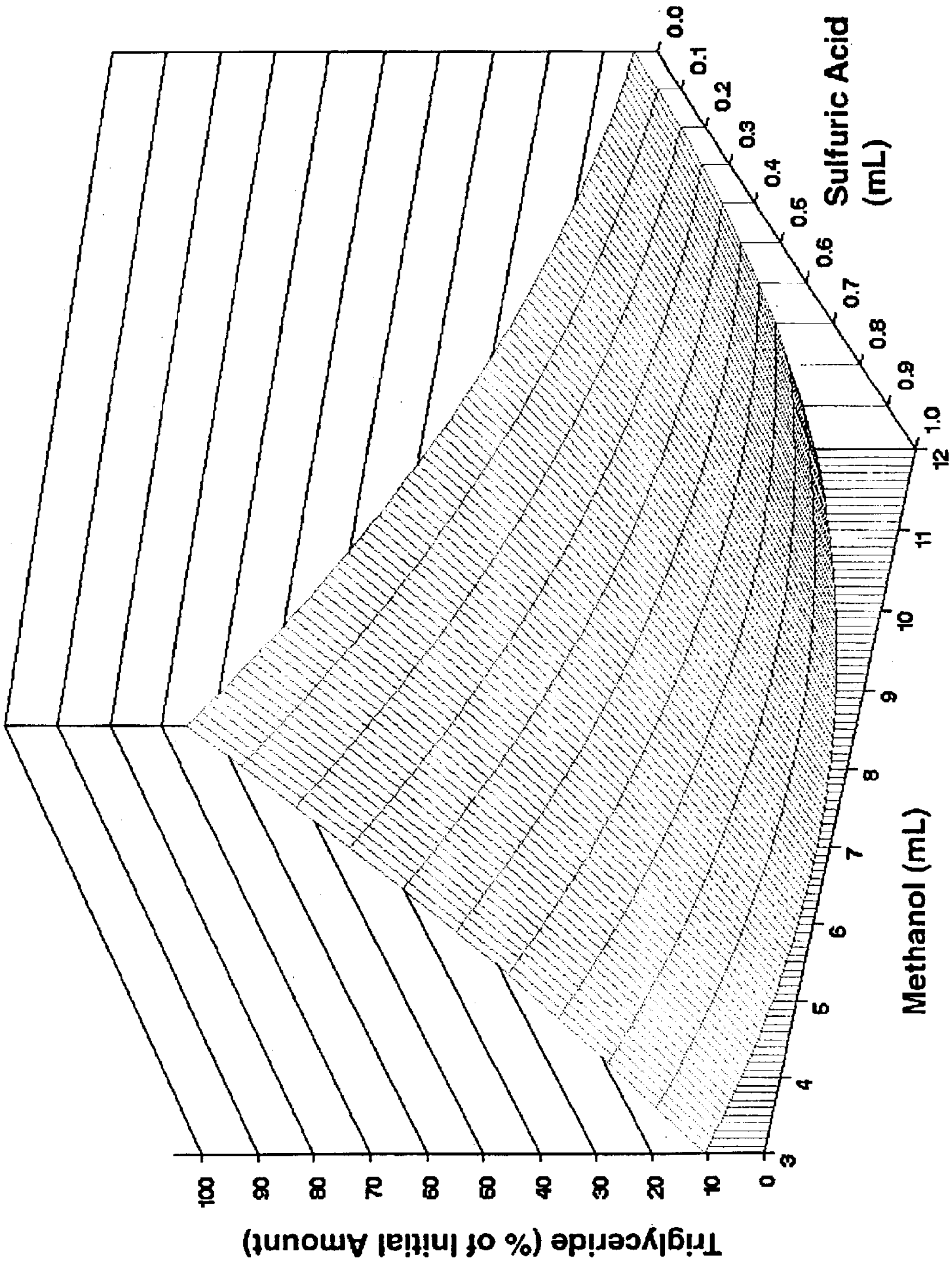

Seven to 8 mL of methanol per 5.00 g acid oil was indicated as giving optimal FFA esterification, with higher residual FFA levels above and below this value (FIG. 1A). Unreacted FFA levels were lower at the higher sulfuric acid concentrations used (FIG. 1A). A similar optimal methanol level existed for DAG esterification, and was also achieved at the higher sulfuric acid levels used (FIG. 1B). Residual DAG increased noticeably at low methanol concentrations, particularly when accompanied by low sulfuric acid levels (FIG. 1B). For TAG (FIG. 1C), the lowest residual levels were seen in reactions containing the maximum amounts of methanol tested (12 mL per 5.00 g acid oil) and sulfuric acid levels of approximately 0.3 mL. Increased amounts of sulfuric acid (1 mL) gave residual TAG comparable to this minimum value in reactions containing only 7.5 mL methanol (FIG. 1C).

By combined analysis of Equations 1–3, the reaction conditions 5.00 g acid oil, 7.5 mL methanol, 1.0 mL sulfuric acid and 26 h incubation at 65° C. were identified as those giving the combined minimum amount of unesterified material. This corresponds to a mole ratio of total FA:methanol:acid of 1:15:1.5. The predicted residual amounts FFA, TAG and DAG under these conditions were 6.6%, 5.8% and 2.6% of input respectively. However, relatively long reaction times were required to reduce the residual levels of unreacted species (FFA, TAG, DAG) to these low levels, and reaction was slow at the longer incubation times. For example, after 15 h of incubation at optimal conditions, the predicted amount of remaining DAG was about 15% of input. A further 5 h incubation reduced this value by only half (data not shown). Similar low esterification rates were seen for FFA and TAG at the longer incubation times. This requirement for relatively long incubations suggests that this method may be of little value industrially.

Production of FAME from high-acid acid oil: Despite the use of a 15-fold molar excess of methanol and relatively long incubations, acid catalyzed esterification was unable to completely eliminate the TAG and DAG in acid oil (as discussed above). As an alternative approach, we investigated the possibility that by completely hydrolyzing the acylglycerols of SS prior to acidulation an acid oil (i.e., high-acid acid oil) readily and completely esterified by acid-catalysis could be prepared.

The injection of steam at pH values exceeding 11 quickly and completely saponified SS (data not shown). Acidulation of the resulting material produced an acid oil with a FFA content of 96.2 wt % and no detectable TAG, DAG or MAG. This resulting HA acid oil was readily esterified by acid catalysis. Through statistical design methods, the relationship of the degree of esterification to the reaction composition and length of incubation at 65° C. was determined. The best-fit second-order response surface to describe the results is given by Equation 4 (terms are as defined above for Equations 1–3):

$$FFA=37.88-38.01\ M-62.69\ A-0.42\ T+15.35\ MA+0.10\ MT+0.72\ AT+12.99\ M^2+96.22\ A^2+0.01\ T^2 \quad (4)$$

Figure 2:
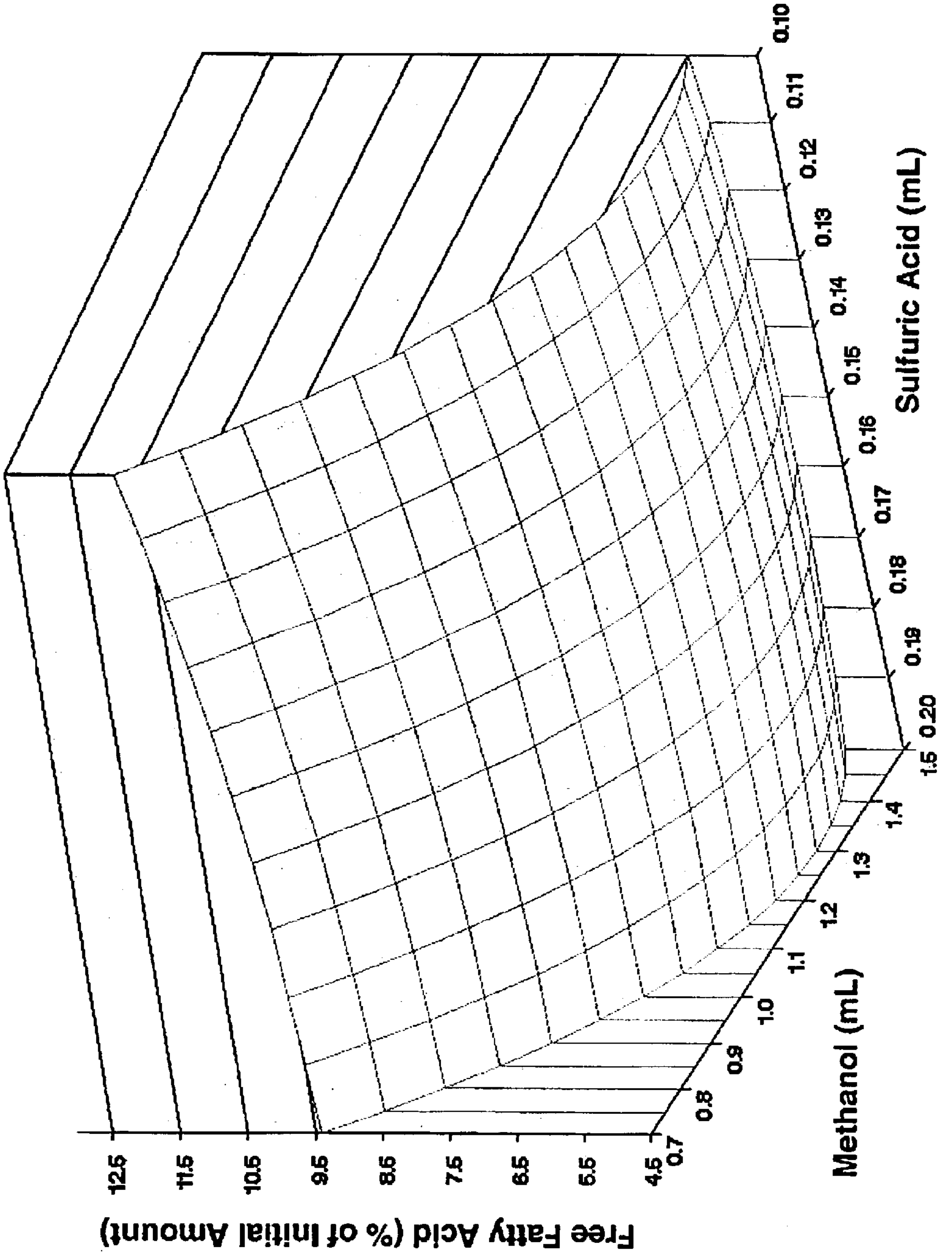
FIG. 2 shows the predicted unreacted free fatty acid levels (% of initial) following the esterification of 5.00 g soybean high-acid acid oil (described below) at 65° C. and 12.5 h, as a function of the inputs of methanol and sulfuric acid. Calculated from Equation 4 below.

This equation fit the experimental data well ($R^2$=0.96). A plot of the relationship of methanol and sulfuric acid concentrations to the level of FFA remaining after 12.5 h esterification, derived from Equation 4, is shown in FIG. 2. This response surface indicates the large impact of changes in methanol concentration, and the smaller role of variations in sulfuric acid concentration, in achieving high-level esterification. Esterification of HA acid oil was initially rapid (during the first hour of incubation), with free fatty acid levels quickly falling to less than 10% of original (data not shown). However, further reduction of the FFA content proceeded slowly, requiring several hours of additional incubation (to a total of about 5 hours) to reach a minimum FFA level of approximately 5% of that originally present. However, surprisingly, this is still substantially less than the 26 h required to achieve the same high degree of esterification with regular acid oil (above).

A canonical analysis of Equation 4 identified 5.00 g HA acid oil, 1.31 mL methanol, 0.17 mL sulfuric acid, and a reaction time of 14 h at 65° C. as the reaction conditions predicted to yield the highest degree of FFA esterification. This represents a molar reactants ratio of FFA:methanol:sulfuric acid of 1:1.8:0.17. Under these conditions, the predicted unreacted FFA level was approximately 5 wt % of input FFA. When 20 g of HA acid oil were incubated under these conditions the yield of FAME was 89% of theoretical. The FFA content of the FAME product was determined by HPLC to be 17 mg/g FAME, which is in acceptable agreement with the value of approximately 50 mg/g predicted by Eqn. 4. The FAME product lacked detectable TAG, DAG and MAG, implying a maximum concentration of approximately 4 mg/g FAME for each of these species. Phytosterols, water, and unidentified materials made up the remaining matter. The identification of a 14 h reaction time as being optimal is essentially academic in nature and may not be important in a commercial process. After 5 hr. of reaction the level of FFA was below 5.5% of input, and the further 9 hr of incubation reduced the FFA level only to approximately 5.0%.

The level of remaining unreacted FFA and acylglycerol is of interest in the context of the use of FAME preparations as engine fuels because these materials affect engine performance and fuel storage stability. For this reason, maximum acceptable levels of these have been established. The accepted specification for biodiesel (Standard Specification for Biodiesel Fuel (B100) Blend Stock for Distillate Fuels, Designation D 6751-02, American Society for Testing and Materials, West Conshohocken, Pa. (2002)) expresses the maximum free fatty acid level in terms of acid number, with a maximum permissible acid number of 0.80 mg KOH/g of biodiesel. Assuming 1:1 stoichiometry in the neutralization of free fatty acids by KOH, this corresponds to a free fatty acid content of 3.91 mg FFA/g soy-derived FAME. The ester preparation synthesized here from HA acid oil under optimal reaction conditions, with an FFA content of 17 mg FFA/g, exceeds the maximum allowed. However, a simple wash protocol involving sequential treatment with aqueous solutions of sodium chloride and hydrated lime was successfully implemented to largely remove these FFA as their calcium salts; as is known in the art, it is possible to utilize other methods to remove the FFA. Methanol was removed from the product under vacuum. The methanol-free ester mixture was then washed three times with 28% by volume of 5 wt % NaCl in tap water; the non-aqueous layer from the last wash was then washed gently with 20% by volume of 4.5 M hydrated lime. The resulting washed FAME sample had a FFA content of 3.5 mg/g, which meets biodiesel specifications. The amount of potential FAME lost by such removal (approx. 5% of input) is acceptable in light of the relative ease, economy, and high degree of esterification of the protocol described herein. In addition, FAME produced from HA acid oil lacked TAG, DAG, and MAG, substances also subject to maximum tolerance specifications in biodiesel (Standard Specification for Biodiesel Fuel (B100) Blend Stock for Distillate Fuels, Designation D 6751-02, American Society for Testing and Materials, West Conshohocken, Pa. (2002)).

As an alternative to the use of multiple washing steps to remove unreacted FFA from the FAME product, a second esterification reaction can be implemented to reduce the level of residual FFA. Water, produced during esterification, is known to inhibit further reaction. Upon partitioning this into two lower layers by centrifugation (6000 g), the upper layer can be again subjected to esterification under the optimal conditions for HA acid oil. The product was centrifuged (6000 g) and the resulting water-soluble lower and middle layers removed. The resulting FAME had a FFA content of 0.4 mg/gm sample, substantially less than the 3.91 mg/g allowed based on the acid value specifications for biodiesel (Standard Specification for Biodiesel Fuel (B100) Blend Stock for Distillate Fuels, Designation D 6751-02, American Society for Testing and Materials, West Conshohocken, Pa. (2002)). The acid value of the resulting material may exceed the allowed value of 0.57 value (NaOH titrant) allowed for biodiesel, due to the presence in the FAME of trace amounts of the sulfuric acid esterification catalyst. By washing for one hour with one volume of NaOH (0.5 N has been used, other concentrations will also suffice) the acid value can be reduced to an acceptable value.

In view of the above, high-acid acid oil is superior to regular acid oil as a feedstock for FAME production since its optimal esterification requires approximately one-eighth the amount of alcohol, one-ninth the amount of acid, occurs in ⅕ to ½ the time, and yields a product low in FFA and lacking residual acylglycerols.

Unexpectedly, the present method does not require an expensive, time-consuming drying of the soapstock, and does not produce a solid sodium sulfate waste stream. Sodium sulfate is produced in the current method during acidulation of the saponified SS; however, it dissolves readily in the water phase formed during acidulation and is removed with that phase. Additional attractive features of the method described herein are that it can be conducted at ambient pressure and at relatively low temperatures. We note that in an industrial setting, conduct of the reaction at the boiling point, with reflux condensation and recovery of methanol, may be advantageous from an engineering standpoint; this should not compromise the speed and efficiency of the process described herein, or the quality of the product. A method such as that described herein should also be effective for the production of FAME from other high-FFA feedstocks.

All of the references cited herein are incorporated by reference in their entirety. Also incorporated by reference in their entirety are the following references: Freedman, B., et al., J. Am. Oil Chem. Soc., 61(10):1638–1643 (1984); Haas, M. J., et al., J. Am. Oil Chem. Soc., 77:373–379 (2000). U.S. Pat. No. 6,399,800 is incorporated by reference in its entirety.

Thus, in view of the above, the present invention concerns (in part) the following:

A method for producing a lipid rich composition comprising (consisting essentially of, consisting of) at least about 80% free fatty acids (or at least about 85% or at least about 90% or at least about 95% or at least about 96% or at least about 97% or at least about 98%), the method comprising (consisting essentially of, consisting of) reacting a feedstock with steam and alkali (sodium hydroxide, potassium hydroxide, or mixtures thereof) at a pH of about 10–about 14 and further reacting said feedstock with steam and sulfuric acid at a pH of about 1–about 2; said method optionally further comprising (consisting essentially of, consisting of) esterifying said lipid rich composition with an alcohol and an inorganic acid catalyst to form a product containing fatty acid alkyl esters.

The above method, wherein said feedstock is soy oil, coconut oil, corn oil, cotton oil, flax oil, palm oil, rapeseed/canola oil, safflower oil, sunflower oil, animal fats, waste greases, soy soapstock, coconut soapstock, corn soapstock, cotton soapstock, flax soapstock, palm soapstock, rapeseed/canola soapstock, safflower soapstock, sunflower soapstock, fully or partially hydrolyzed preparations made from soy, fully or partially hydrolyzed preparations made from coconut, fully or partially hydrolyzed preparations made from corn, fully or partially hydrolyzed preparations made from cotton, fully or partially hydrolyzed preparations made from flax, fully or partially hydrolyzed preparations made from palm, fully or partially hydrolyzed preparations made from rapeseed/canola, fully or partially hydrolyzed preparations made from safflower, fully or partially hydrolyzed preparations made from sunflower, fully or partially hydrolyzed preparations made from animal fats, fully or partially hydrolyzed preparations made from waste greases, or mixtures thereof.

The above method, wherein said feedstock is soy soapstock, coconut soapstock, corn soapstock, cotton soapstock, flax soapstock, palm soapstock, rapeseed/canola soapstock, safflower soapstock, sunflower soapstock, animal fats, waste greases, or mixtures thereof.

The above method, wherein said feedstock is soy soapstock, rapeseed/canola soapstock, or mixtures thereof.

The above method, wherein said feedstock is soy soapstock.

The above method further comprising esterifying said lipid rich composition comprising at least about 80% free fatty acids with an alcohol ($C_{1-4}$ alcohol such as methanol, ethanol, isopropanol, or mixtures thereof) and an inorganic acid catalyst (sulfuric acid, phosphoric acid, hydrochloric acid, or mixtures thereof) to form a product containing fatty acid alkyl esters.

The above method, wherein the product contains less than about 100 mg FFA/g fatty acid alkyl esters or contains less than about 60 mg FFA/g fatty acid alkyl esters or contains less than about 51 mg FFA/g fatty acid alkyl esters or contains less than about 17 mg FFA/g fatty acid alkyl esters contains less than about 10 mg FFA/g fatty acid alkyl esters or contains less than about 4 mg FFA/g fatty acid alkyl esters.

The above method, wherein the product contains less than about 0.1% weight basis of unreacted triacylglycerols, unreacted diacylglycerols, and unreacted monoacylglycerols or contains less than about 0.04% weight basis of unreacted triacylglycerols, unreacted diacylglycerols, and unreacted monoacylglycerols.

The above method, wherein the product contains fatty acid methyl esters or contains fatty acid ethyl esters.

The above method, wherein the alcohol is a $C_{1-4}$ alcohol or is selected from the group consisting of methanol, ethanol, isopropanol, and mixtures thereof, or is selected from the group consisting of methanol, ethanol, and mixtures thereof, or is ethanol or methanol.

The above method, wherein the inorganic acid catalyst is selected from the group consisting of sulfuric acid, phosphoric acid, hydrochloric acid, or mixtures thereof, or is sulfuric acid.

The above method, wherein the alkali is selected from the group consisting of NaOH, KOH, or mixtures thereof, or is NaOH.

The above method, further comprising washing said fatty acid alkyl esters (e.g., with NaCl and then with $Ca(OH)_2$).

The above method, further comprising the recovery of the FAME fraction after the initial esterification and subjecting it to a second esterification reaction.

A lipid rich composition comprising (consisting essentially of, consisting of) at least about 80% free fatty acids (or at least about 85% or at least about 90% or at least about 95% or at least about 96% or at least about 97% or at least about 98%).

A lipid rich composition comprising (consisting essentially of, consisting of) at least about 80% free fatty acids (or at least about 85% or at least about 90% or at least about 95% or at least about 96% or at least about 97% or at least about 98%), said composition produced by a method comprising (consisting essentially of, consisting of) reacting a feedstock with steam and alkali (sodium hydroxide, potassium hydroxide, or mixtures thereof) at a pH of about 10–about 14 and further reacting said feedstock with steam and sulfuric acid at a pH of about 1–about 2.

A method for producing fatty acid alkyl esters, comprising (consisting essentially of, consisting of) esterifying a material containing free fatty acids with an alcohol and an inorganic acid catalyst to form a product containing fatty acid alkyl esters, wherein (i) the material contains at least about 40% FFA and is produced by reacting a feedstock with steam and sulfuric acid at a pH of about 1–about 2 or (ii) the material contains at least about 80% FFA and is produced by reacting a feedstock with steam and alkali at a pH of about 10–about 14 and further reacting the feedstock with steam and sulfuric acid at a pH of about 1–about 2.

The above method, wherein the product contains less than about 100 mg FFA/g fatty acid alkyl esters or contains less than about 60 mg FFA/g fatty acid alkyl esters or contains less than about 51 mg FFA/g fatty acid alkyl esters or contains less than about 17 mg FFA/g fatty acid alkyl esters contains less than about 10 mg FFA/g fatty acid alkyl esters or contains less than about 4 mg FFA/g fatty acid alkyl esters.

The above method, wherein the product contains less than about 0.1% weight basis of unreacted triacylglycerols, unreacted diacylglycerols, and unreacted monoacylglycerols or contains less than about 0.04% weight basis of unreacted triacylglycerols, unreacted diacylglycerols, and unreacted monoacylglycerols.

The above method, wherein the product contains fatty acid methyl esters or fatty acid ethyl esters.

The above method, wherein the alcohol is a $C_{1-4}$ alcohol or is selected from the group consisting of methanol, ethanol, isopropanol, and mixtures thereof, or is selected from the group consisting of methanol, ethanol, and mixtures thereof, or is ethanol or methanol.

The above method, wherein the inorganic acid catalyst is selected from the group consisting of sulfuric acid, phosphoric acid, hydrochloric acid, or mixtures thereof, or is sulfuric acid.

The above method, wherein the alkali is selected from the group consisting of NaOH, KOH, or mixtures thereof, or is NaOH.

The above method, wherein (i) the material contains at least about 40% FFA (or 45% or 50% or 55% or 60% or 65% or 70%) and is produced by reacting a feedstock with steam and sulfuric acid at a pH of about 1–about 2.

The above method, wherein (ii) the material contains at least about 80% FFA (or 85% or 90% or 95% or 96% or 97% or 98%) and is produced by reacting a feedstock with steam and alkali at a pH of about 10–about 14 and further reacting said feedstock with steam and sulfuric acid at a pH of about 1–about 2.

The above method, further comprising washing said fatty acid alkyl esters (e.g., with NaCl and then with $Ca(OH)_2$).

The above method, further comprising the recovery of the FAME fraction after the initial esterification and subjecting it to a second esterification reaction.

The above method, wherein said feedstock is soy oil, coconut oil, corn oil, cotton oil, flax oil, palm oil, rapeseed/canola oil, safflower oil, sunflower oil, animal fats, waste greases, soy soapstock, coconut soapstock, corn soapstock, cotton soapstock, flax soapstock, palm soapstock, rapeseed/canola soapstock, safflower soapstock, sunflower soapstock, fully or partially hydrolyzed preparations made from soy, fully or partially hydrolyzed preparations made from coconut, fully or partially hydrolyzed preparations made from corn, fully or partially hydrolyzed preparations made from cotton, fully or partially hydrolyzed preparations made from flax, fully or partially hydrolyzed preparations made from palm, fully or partially hydrolyzed preparations made from rapeseed/canola, fully or partially hydrolyzed preparations made from safflower, fully or partially hydrolyzed preparations made from sunflower, fully or partially hydrolyzed preparations made from animal fats, fully or partially hydrolyzed preparations made from waste greases, or mixtures thereof.

The above method, wherein said feedstock is soy soapstock, coconut soapstock, corn soapstock, cotton soapstock, flax soapstock, palm soapstock, rapeseed/canola soapstock, safflower soapstock, sunflower soapstock, animal fats, waste greases, or mixtures thereof.

The above method, wherein said feedstock is soy soapstock, rapeseed/canola soapstock, or mixtures thereof.

The above method, wherein said feedstock is soy soapstock.

Fatty acid alkyl esters produced by a method comprising (consisting essentially of, consisting of) esterifying a material containing free fatty acids with an alcohol and an inorganic acid catalyst to form a product containing fatty acid alkyl esters, wherein (i) the material contains at least about 40% FFA and is produced by reacting a feedstock with steam and sulfuric acid at a pH of about 1–about 2 or (ii) the material contains at least about 80% FFA and is produced by reacting a feedstock with steam and alkali at a pH of about 10–about 14 and further reacting the feedstock with steam and sulfuric acid at a pH of about 1–about 2.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for producing a lipid rich composition comprising at least about 80% free fatty acids, said method comprising reacting a feedstock with steam and alkali at a pH of about 10–about 14 and further reacting said feedstock with steam and sulfuric acid at a pH of about 1–about 2; said method optionally further comprising esterifying said lipid rich composition with an alcohol and an inorganic acid catalyst to form a product containing fatty acid alkyl esters.

2. The method according to claim 1, wherein said lipid rich composition comprises at least about 85% FFA.

3. The method according to claim 1, wherein said lipid rich composition comprises at least about 90% FFA.

4. The method according to claim 1, wherein said lipid rich composition comprises at least about 95% FFA.

5. The method according to claim 1, wherein said lipid rich composition comprises at least about 96% FFA.

6. The method according to claim 1, wherein said lipid rich composition comprises at least about 97% FFA.

7. The method according to claim 1, wherein said lipid rich composition comprises at least about 98% FFA.

8. The method according to claim 1, wherein said alkali is selected from the group consisting of sodium hydroxide, potassium hydroxide, and mixtures thereof.

9. The method according to claim 1, wherein said feedstock is soy oil, coconut oil, corn oil, cotton oil, flax oil, palm oil, rapeseed/canola oil, safflower oil, sunflower oil, animal fats, waste greases, soy soapstock, coconut soapstock, corn soapstock, cotton soapstock, flax soapstock, palm soapstock, rapeseed/canola soapstock, safflower soapstock, sunflower soapstock, fully or partially hydrolyzed preparations made from soy, fully or partially hydrolyzed preparations made from coconut, fully or partially hydrolyzed preparations made from corn, fully or partially hydrolyzed preparations made from cotton, fully or partially hydrolyzed preparations made from flax, fully or partially hydrolyzed preparations made from palm, fully or partially hydrolyzed preparations made from rapeseed/canola, fully or partially hydrolyzed preparations made from safflower, fully or partially hydrolyzed preparations made from sunflower, fully or partially hydrolyzed preparations made from animal fats, fully or partially hydrolyzed preparations made from waste greases, or mixtures thereof.

10. The method according to claim 1, wherein said feedstock is soy soapstock, coconut soapstock, corn soapstock, cotton soapstock, flax soapstock, palm soapstock, rapeseed/canola soapstock, safflower soapstock, sunflower soapstock, animal fats, waste greases, or mixtures thereof.

11. The method according to claim 1, wherein said feedstock is soy soapstock, rapeseed/canola soapstock, or mixtures thereof.

12. The method according to claim 1, wherein said feedstock is soy soapstock.

13. The method according to claim 1, said method further comprising esterifying said lipid rich composition with an alcohol and an inorganic acid catalyst to form a product containing fatty acid alkyl esters.

14. A lipid rich composition comprising at least about 80% free fatty acids.

15. A lipid rich composition comprising at least about 80% free fatty acids, said composition produced by a method comprising reacting a feedstock with steam and alkali at a pH of about 10–about 14 and further reacting said feedstock with steam and sulfuric acid at a pH of about 1–about 2.

16. A method for producing fatty acid alkyl esters, comprising esterifying a material containing free fatty acids with an alcohol and an inorganic acid catalyst to form a product containing fatty acid alkyl esters, wherein (i) said material contains at least about 40% FFA and is produced by reacting a feedstock with steam and sulfuric acid at a pH of about 1–about 2 or (ii) said material contains at least about 80% FFA and is produced by reacting a feedstock with steam and alkali at a pH of about 10–about 14 and further reacting said feedstock with steam and sulfuric acid at a pH of about 1–about 2.

17. The method according to claim 16, wherein said alcohol is a $C_{1-4}$ alcohol.

18. The method according to claim 16, wherein said inorganic acid catalyst is selected from the group consisting of sulfuric acid, phosphoric acid, hydrochloric acid, or mixtures thereof.

19. The method according to claim 16, wherein said alkali is selected from the group consisting of NaOH, KOH, or mixtures thereof.

20. The method according to claim 16, wherein (i) said material contains at least about 40% FFA and is produced by reacting a feedstock with steam and sulfuric acid at a pH of about 1–about 2.

21. The method according to claim 16, wherein (ii) said material contains at least about 80% FFA and is produced by reacting a feedstock with steam and alkali at a pH of about 10–about 14 and further reacting said feedstock with steam and sulfuric acid at a pH of about 1–about 2.

22. The method according to claim 16, further comprising washing said fatty acid alkyl esters.

23. The method according to claim 16, further comprising washing said fatty acid alkyl esters with NaCl and then with $Ca(OH)_2$.

24. The method according to claim 16, wherein said feedstock is soy oil, coconut oil, corn oil, cotton oil, flax oil, palm oil, rapeseed/canola oil, safflower oil, sunflower oil, animal fats, waste greases, soy soapstock, coconut soapstock, corn soapstock, cotton soapstock, flax soapstock, palm soapstock, rapeseed/canola soapstock, safflower soapstock, sunflower soapstock, fully or partially hydrolyzed preparations made from soy, fully or partially hydrolyzed preparations made from coconut, fully or partially hydrolyzed preparations made from corn, fully or partially hydrolyzed preparations made from cotton, fully or partially hydrolyzed preparations made from flax, fully or partially hydrolyzed preparations made from palm, fully or partially hydrolyzed preparations made from rapeseed/canola, fully or partially hydrolyzed preparations made from safflower, fully or partially hydrolyzed preparations made from sunflower, fully or partially hydrolyzed preparations made from animal fats, fully or partially hydrolyzed preparations made from waste greases, or mixtures thereof.

25. The method according to claim 16, wherein said feedstock is soy soapstock, coconut soapstock, corn soapstock, cotton soapstock, flax soapstock, palm soapstock, rapeseed/canola soapstock, safflower soapstock, sunflower soapstock, animal fats, waste greases, or mixtures thereof.

26. The method according to claim 16, wherein said feedstock is soy soapstock, rapeseed/canola soapstock, or mixtures thereof.

27. The method according to claim 16, wherein said feedstock is soy soapstock.

28. The method according to claim 1, said method comprising reacting said feedstock with steam and alkali at a pH of about 11–about 14.

29. The method according to claim 1, said method comprising reacting said feedstock with steam and alkali at a pH of about 11.5–about 14.

30. The method according to claim 1, said method comprising reacting said feedstock with steam and alkali at a pH of about 13–about 14.

31. The method according to claim 1, said method comprising further reacting said feedstock with steam and sulfuric acid at a pH of about 1.6.

* * * * *